United States Patent [19]
Shiraishi et al.

[11] Patent Number: 5,888,237
[45] Date of Patent: Mar. 30, 1999

[54] ARTIFICIAL LIMB INCLUDING AIR CYLINDER DEVICE

[75] Inventors: Norio Shiraishi; Yasukazu Furuichi; Kazuo Nakatani; Masahiko Okuda, all of Kobe, Japan

[73] Assignee: Nabco Limited, Kobe, Japan

[21] Appl. No.: 951,781

[22] Filed: Oct. 16, 1997

[51] Int. Cl.$^6$ ........................................ A61F 2/64
[52] U.S. Cl. ............................... 623/44; 623/43
[58] Field of Search ........................... 623/39–46

[56] References Cited

U.S. PATENT DOCUMENTS

| 5,018,514 | 5/1991 | Grood et al. ................ 623/39 X |
| 5,728,172 | 3/1998 | Krieger ............................ 623/44 |

FOREIGN PATENT DOCUMENTS

| 42 32 602 A1 | 3/1994 | Germany ......................... 623/39 |

*Primary Examiner*—David H. Willse
*Attorney, Agent, or Firm*—Kane,Dalsimer,Sullivan, Kurucz, Levy,Eisele and Richard, LLP

[57] ABSTRACT

An artificial limb provides for positional relation between a first pin for rotatably connecting one end of an air cylinder device to a lower member and a second pin for rotatably connecting the other end of the air cylinder device to an upper member. The attaching position of the second pin is set to satisfy certain predetermined conditions when an artificial limb is in a completely extended state. The position of an air cylinder device (particularly, the attaching position of the second pin) is changed in conformity with a walking speed which is variable in phase such as normal walking, quick walking, and running with small steps. The artificial limb further comprises a pin position change capable of changing the position of a second pin rotatably connected to an upper member in conformity with variation of walking speed. A first example of the pin position change includes a plurality of attachment holes formed on the knee plate of the upper member and the position of the second pin is changed by attaching the second pin selectively to one of the attachment holes. If it is designed such that an elongate hole is formed along a circular arc so that the attaching position to the elongate hole can be changed, the position of the second pin can be changed steplessly or successively.

10 Claims, 12 Drawing Sheets

ARTIFICIAL LIMB INCLUDING AIR CYLINDER DEVICE

BACKGROUND OF THE INVENTION

This invention relates to a prosthetic limb utilizing an air cylinder device for assisting a bending and extending action of the knee, and more particularly to a technology capable of enlarging an effective stroke of an air cylinder device and effective in making a prosthetic limb small in size or in obtaining a motion in conformity with a walking speed of the user.

In general, artificial limbs accompanying with a bending and extending action of the knee comprises an upper member including a knee plate to which a load or weight of the user (amputee) applies, a lower member connected to the upper member at the knee portion, a knee axis rotatably connecting the upper and lower members together, and in addition, an auxiliary means for assisting a bending and extending action of the knee. One typical example of this type of prosthetic leg is an above-knee prosthesis which includes a socket supported on an upper end of the knee plate of the upper member and adapted to receive the stump therein, and a foot member supported on a lower end of the lower member.

A hydraulic cylinder device or an air cylinder device is used as the auxiliary means for assisting a bending and extending action of the knee. U.S. Pat. No. 2,859,451 discloses a prosthetic leg utilizing a hydraulic cylinder device, and U.S. Pat. No. 5,405,407 discloses a prosthetic leg utilizing an air cylinder device. The hydraulic cylinder device and the air cylinder device are different in fluid to be used but the same in function for assisting a bending and extending action of the knee, thereby giving a walking style resembling a natural walk to the prosthetic leg.

Comparing the hydraulic cylinder device with the air cylinder device both as an auxiliary means, an oil as a working fluid of the hydraulic cylinder device has almost no compressive properties. In contrast, an air as a working fluid of the air cylinder device has compressive properties. Therefore, according to the air cylinder device, a repulsive force can be obtained by a compressed energy generated by compressing the air after the knee is bent maximum. In order to effectively utilize such features of the air cylinder device, it is necessary to enlarge an effective stroke of the cylinder. However, any attempt to enlarge an effective stroke of the cylinder is encountered with a difficulty in which the attempt tends to enlarge the size of the prosthetic leg. For this reason, not many specific proposals were made until today for enlarging the effective stroke of the air cylinder device in this type of a prosthetic leg. For example, specific proposals are seen in the above-discussed US patents which teach that if a rod end side of the cylinder device is connected to the upper member through a pin, an available space around the knee will be increased. Also, Japanese Laid-Open Patent Application No. 551/1997 teaches an improvement of U.S. Pat. No. 5,405,407. What is illustrated in the drawings of this laid-open application is only such a very general knowledge that a connecting position of a pin on the rod end side is located backwardly of the knee axis. FIG. 2 of U.S. Pat. No. 2,859,451 and FIG. 4 of Japanese Laid-Open Patent Application No. 551/1997 show a connecting position of a pin on the rod end side which position is located backward and slightly upward of the knee axis. However, they merely show the connecting position of the pin in the drawings and none of them particularly specifies the connecting position. In addition, none of them teaches the technical significance of the connecting position of the pin.

SUMMARY OF THE INVENTION

It is the first object of the present invention to apply a technology capable of contribution to a miniaturization of a prosthetic limb which technology is capable of increasing an amount of work of an air cylinder device while making the air cylinder smaller in size, by effectively utilizing the ability of the air cylinder device.

To achieve this first object, according to the present invention, a positional relation between a first pin for rotatably connecting one end of an air cylinder device to a lower member and a second pin for rotatably connecting the other end of the air cylinder device to an upper member, particularly an attaching position of the second pin is set to satisfy the conditions under the item A listed below, when an artificial limb is in a completely extended state.

A. When a tangential line is drawn from the first pin with respect to a trajectory of rotation of the second pin which rotates about a knee axis for rotatably connecting the upper member and the lower member together, a point of contact of the tangential line is located at the center of a range of swinging of the second pin caused by walking of the user.

When the conditions under this item A are satisfied, a piston of the air cylinder device becomes the maximum speed at the center of the range of swinging of the second pin caused by walking of the user and therefore, an overall amount of work performed in accordance with a motion of the piston. This makes it possible to increase a compressed energy of air within the air cylinder device. And a repulsive force after bending of the knee can be increased effectively by the increased compressed energy.

The air cylinder device includes a piston for partitioning an interior of a cylinder body into a first chamber on the bottom side and second chamber on the head side, and a rod one end of which is integral with the piston and the other end of which extends outwardly from the head side of the cylinder body. In order to reduce the space required around the knee, the second pin is preferably located at an end portion of the rod. Also, the second pin is preferably located at a rear part of the knee. The reason is that by doing so, it becomes advantageous not only to arrange a brake means around the axis of the knee but also to receive the cylinder body of the air cylinder device in a hollow interior of a frame and as a result, an outer appearance of the prosthetic limb can be improved.

The range of swinging of the second pin is about 60 degrees when the walking speed is in a range from a slow walking to a normal walking, about 70 degrees when the walking speed is a quick walking, and about 80 degrees when the walking speed is a run with short steps (trot). Therefore, the range of swinging of the second pin variable in accordance the walking phase is, in general, within a range from about 60 degrees to about 80 degrees. Ideally, the attaching position of the second pin is changed in conformity with variation of the walking speed, so that the aforementioned conditions under the item A are always satisfied. As a secondary measure, the range of swinging of the second pin is set such that the attaching position of the second pin is desirably steppingly selected in conformity with each walking speed which is varied from 2 steps to 4 steps (typically three steps of 60 degrees, 70 degrees and 80 degrees), for example.

It is, therefore, a second object of the present invention, to provide a technology capable of changing the attaching position of an air cylinder device (particularly, attaching position of the second pin) in conformity with a walking speed which is variable in phase such as normal walking, quick walking, and run with small steps.

In order to achieve the second object, an artificial limb including an air cylinder device according to the present invention comprises pin position change means capable of changing the position of a second pin rotatably connected to an upper member in conformity with variation of walking speed. A first example of the pin position change means includes a plurality of attachment holes formed on a knee plate of the upper member and the position of the second pin is changed by attaching the second pin selectively to one of the attachment holes. It is preferred that a plurality of attachment holes are arranged on an arc of a circle drawn about the axis of the knee, so that the space around the knee can be reduced as much as possible. This first example, in which the second pin is attached to one of the attachment holes, can easily be practiced by changing a part of the conventional prosthetic leg. Similarly, a second example of a pin position change means includes an elongate hole formed in a knee plate of the upper member and the second pin is movable along and securable to this elongate hole, so that the position of the second pin can be changed. The elongate hole of this second example is preferably arranged, as each hole of the first example, along an arc of a circle drawn around the axis of the knee. The second example can easily be practiced as the first example. In addition, the position of the second pin can be changed steplessly or successively. In the first and second examples, it is necessary to do such a job as to remove the second pin from one of the attachment holes and attach it to another attachment hole, or such a job as to loosen the second pin, move it from a first position to a second position in the elongate hole, and then tighten it again.

It is the third object of the present invention to provide a technology capable of automatically changing the position of the second pin without such a need of attaching and removing the second pin.

In order to achieve the third object, according to the present invention, the second pin is supported on a prescribed area, (in general, one end portion of the rod) of the air cylinder, and then, the second pin is connected to the upper member through a certain connecting means. The certain connecting means includes a hydraulic cylinder supported by the upper member and capable of changing the position of the inside piston in conformity with a walking speed,land a link mechanism for inter-linking the hydraulic cylinder and the second pin. The hydraulic cylinder contains therein a piston for partitioning the interior into two chambers, a spring for biasing the piston in a certain direction, and flow control means provided on the piston. The flow control means comprises two fluid flow paths for inter-communicating the two chambers partitioned by the piston, a throttle valve and a check valve which are provided on one of the fluid flow paths, and another check valve provided on the other fluid flow path. The flow control means changes the position of the piston by appropriately breaking a balancing relation with the force of the spring in conformity with a repulsive force of the air cylinder device, namely, walking speed. Therefore, the hydraulic cylinder is capable of changing the position of the second pin based on a change in position of the internal piston through the link mechanism and also capable of changing the position of the second pin successively and automatically in conformity with a walking speed.

DETAILED DESCRIPTION OF PREFERRED EMBODIMENTS

Figure 1:
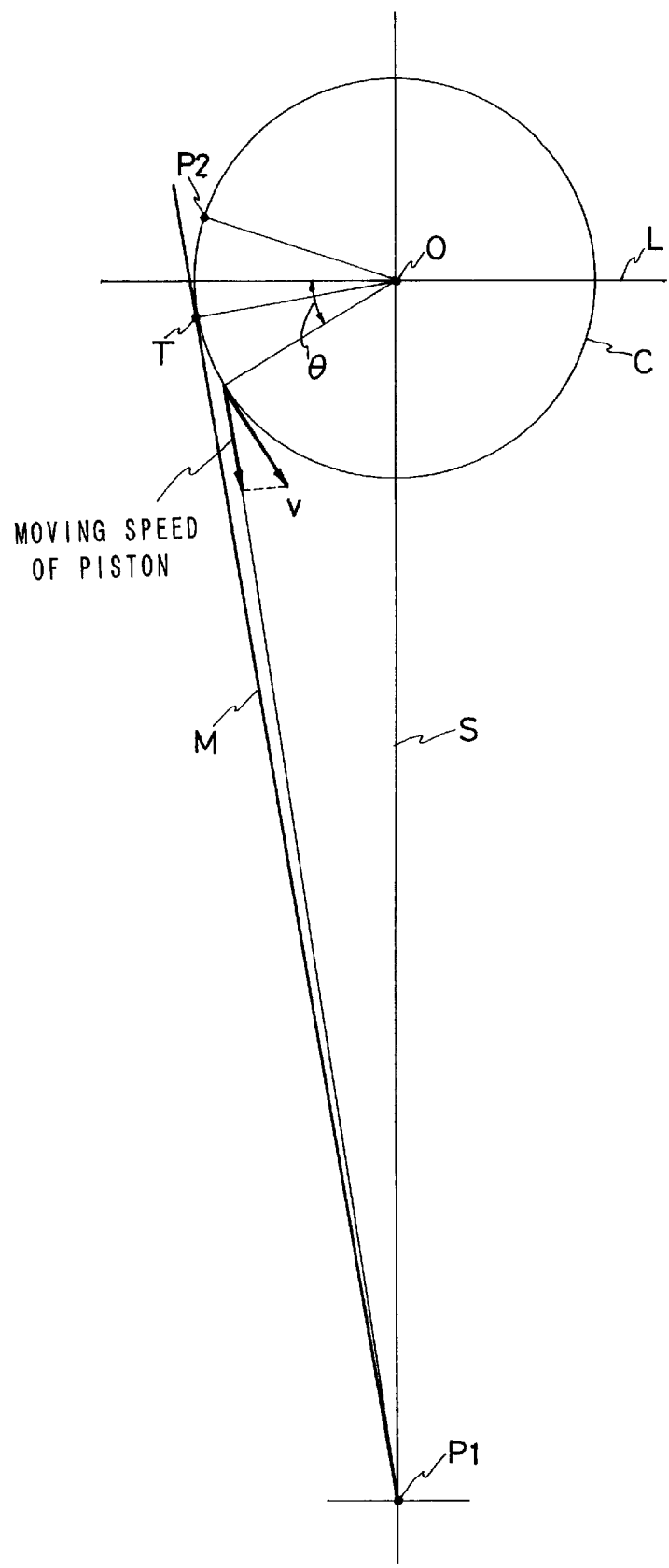
FIG. 1 is a diagram for explaining the basic principles of the present invention.
Figure 2:
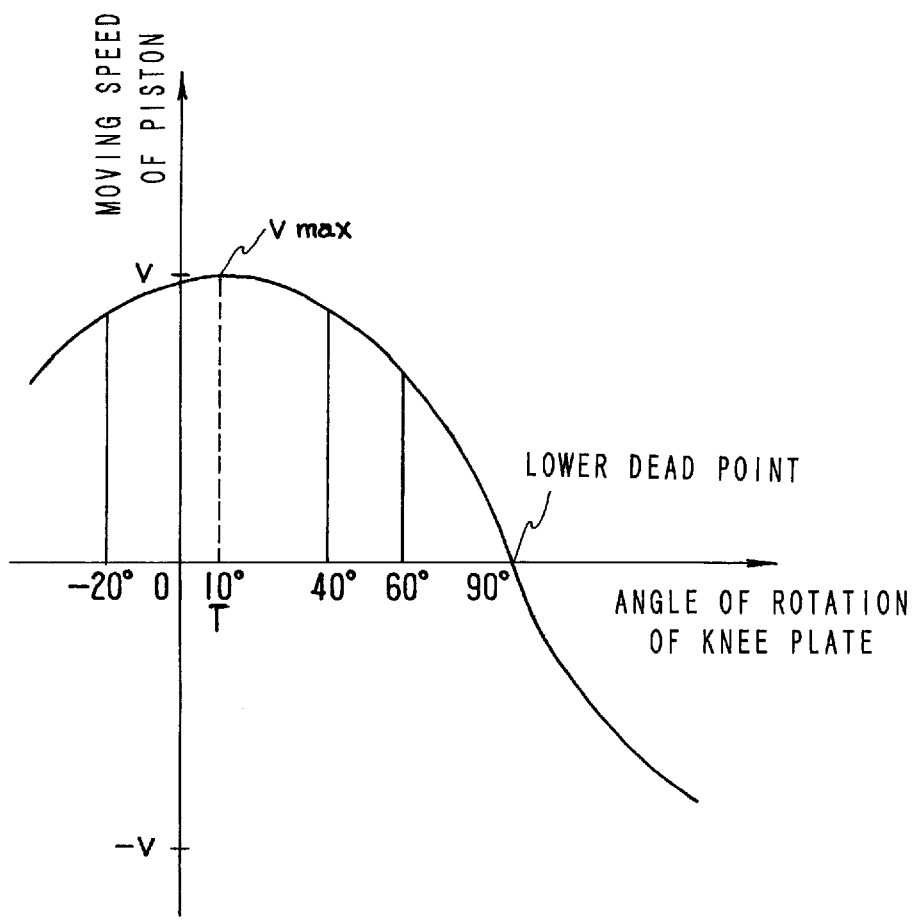
FIG. 2 is a characteristic chart for further explaining the basic principles of the present invention, and shows a relation between an angle of rotation of a knee plate and a speed of movement of a piston.

Referring first to FIGS. 1 and 2, basic principles of the present invention will be described.

In FIG. 1, a point O indicates the center (i.e., axis of a knee plate) of an axis of the knee for rotatably connecting an upper member including a knee plate to which a load of the user is applied to a lower member corresponding to a lower limb. An air cylinder device for assisting a walking includes a connecting point (center of a first pin) P1 with respect to the lower member, and another connecting point (center of a second pin) P2 with respect to the knee plate of the upper member. When the knee plate is swung as the user walks, the center P2 of the second pin moves on a circle C drawn about the axis O of the knee plate. That is, the circle C is a trajectory of rotation of the center P2 of the second pin. On the other hand, an axis of the prosthetic limb is obtained by connecting the center P1 of the first pin to the axis O of the knee plate.

A line denoted by reference character L extends through the axis O of the knee plate and intersects a center axis S at right angles. The position of the center P2 of the second pin is expressed by an angle $\theta$ with reference to the line L. Irrespective of the value of the angle $\theta$, the rotational speed of the center P2 of the second pin is constant and can be considered to take a value v normally. On the other hand, the moving speed of the piston of the air cylinder device becomes maximum at a particular position T and varies in the vicinity of this particular position T. The position T where the moving speed of the piston becomes maximum corresponds to a point of contact of a tangential line M drawn from the center P1 of the first pin with respect to the circle C. As shown in a characteristic view of FIG. 2, the moving speed of the piston becomes maximum at the particular position T and varies in such a manner as to exhibit a sine curve in accordance with rotation of the piston. In order to make an amount of overall work maximum, it is necessary to set such that the moving speed of the piston becomes maximum at the center of the range of swinging of the second pin caused by walking.

According to the result of measurement or according to the teaching of experiences, the center P2 of the second pin is swung in a range of from about 60 degrees to about 80 degrees as the user walks. More specifically, the range of swinging of the second pin is such that it swings about 60 degrees when it corresponds to a walking speed from a slow walking to a normal walking, about 70 degrees when it corresponds to the speed of a quick walking, and about 80 degrees when it corresponds to the speed of run with small steps. Therefore, if the capability of the air cylinder device is to be effectively utilized during a normal walking, the point T is a position where the angle $\theta$ is about 10 degrees in case of an artificial limb of a typical size (for example, the distance from the point O to the point P1 is about 165 mm, and the distance from the point O to the point P2 is about 30 mm). In view of the foregoing, 60 degrees as a value of an angle of swinging is divided into two equal parts so that a front part of the point T may have 30 degrees of an angle of swinging and a rear part of the point T may have the remaining 30 degrees of an angle of swinging. As a consequence, when the artificial limb is in a completely extended state, the center P2 of the second pin is set to a position where $\theta$=about −20 degrees. In this respect, heretofore, it was customary that the center P2 of the second pin is set to a position where $\theta$=0 degree which fails to effectively utilize the stroke of the piston of the air cylinder device. The principles of the present invention has hereinbefore been described. The basic idea of the present invention is that when the artificial limb is in a completely extended state, the center P2 of the second pin is set to a particular position, thereby increasing an amount of work of the air cylinder device as much as possible. According to the present invention, this basic idea is further progressed one step so that it includes an idea that the center P2 of the second pin is appropriately changed in accordance with the change in speed of walking.

Figure 3:
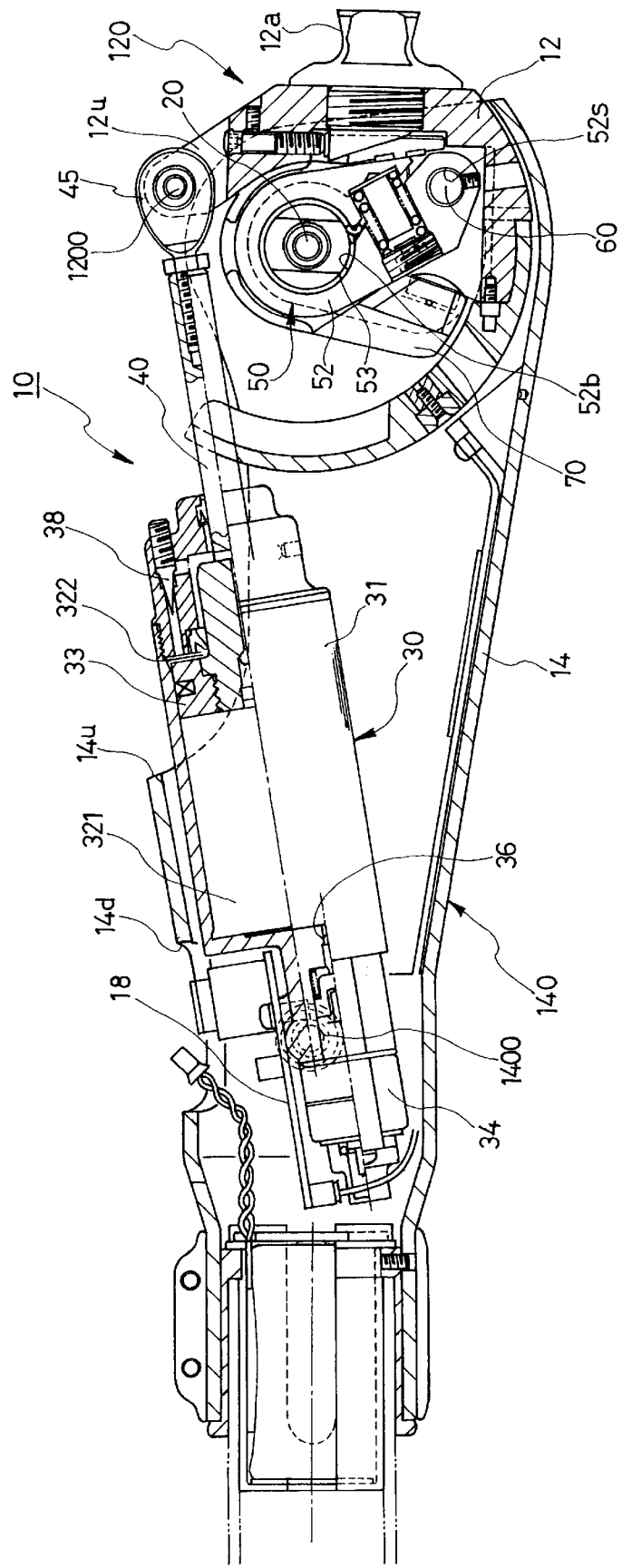
FIG. 3 is a view showing an overall construction of a thigh prosthetic limb incorporated with the present invention and is a sectional view when the knee is extended.
Figure 4:
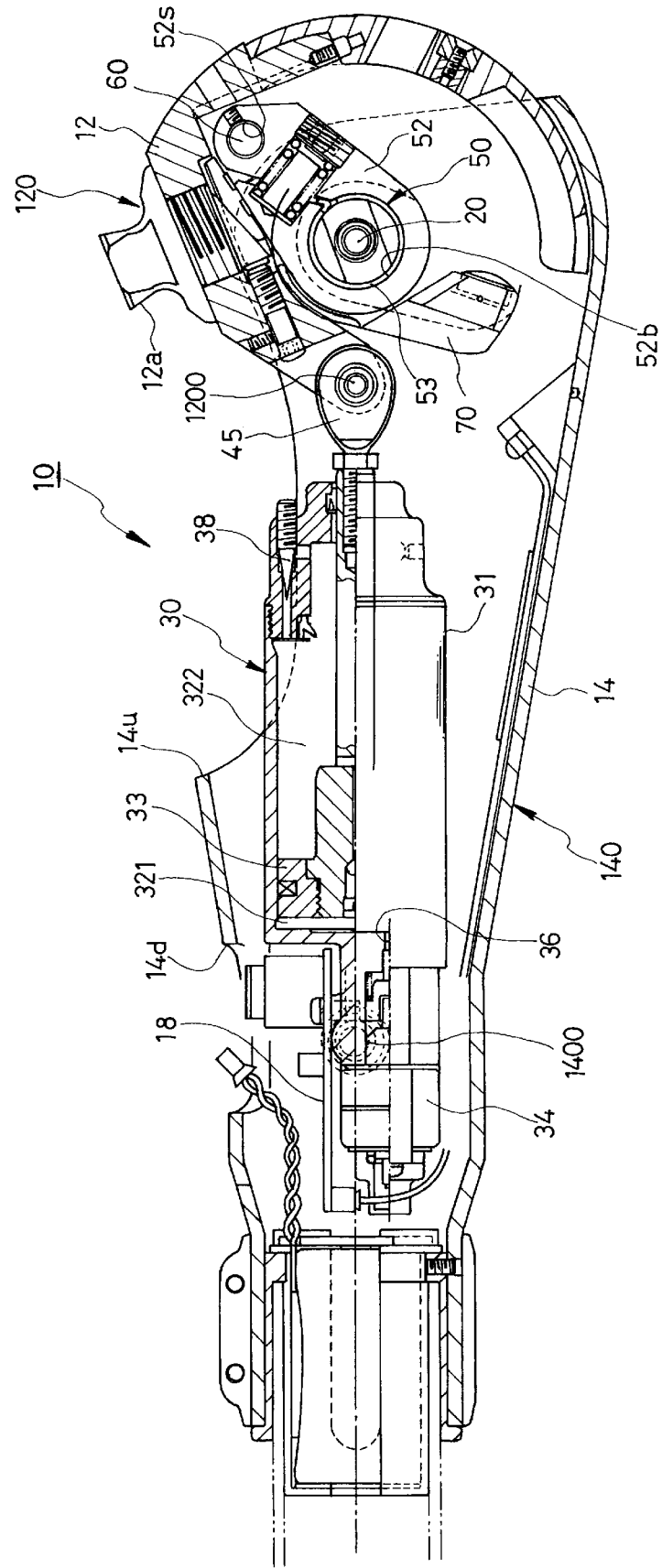
FIG. 4 is a sectional view showing a bending state of the thigh prosthetic limb of FIG. 3.

Referring now to FIGS. 3 and 4, an overall construction of a thigh prosthetic leg 10 incorporated with the present invention will be described.

The thigh prosthetic leg 10 is for persons who lost their thighs. The thigh prosthetic leg 10 comprises an upper member 120 including a knee plate 12 having a knee-like configuration, a lower member 140 chiefly consisting of a hollow frame 14 which extends from the knee portion to the foot portion, and a knee axis 20 for rotatably connecting the lower member 140 and the upper member 120 together at the knee portion. The knee plate 12 is made of an aluminum alloy on a part of which a connecting portion 12a for connecting a socket, not shown, is integrally supported. On the other hand, the hollow frame 14, which is a chief component part of the lower member 140, is made of a fiber-reinforced plastic having a thickness of about 3 mm. The hollow frame 14 is provided at a rear portion thereof with an upper and a lower opening 14u, 14d. The upper opening 14u is an opening through which parts can be set up within the frame 14 or an opening for avoiding interference between the air cylinder device 30 and the frame 14. The lower opening 14d is an opening for establishing an electrical connection with an electronic board 18 which is disposed within the frame 14.

Figure 5:
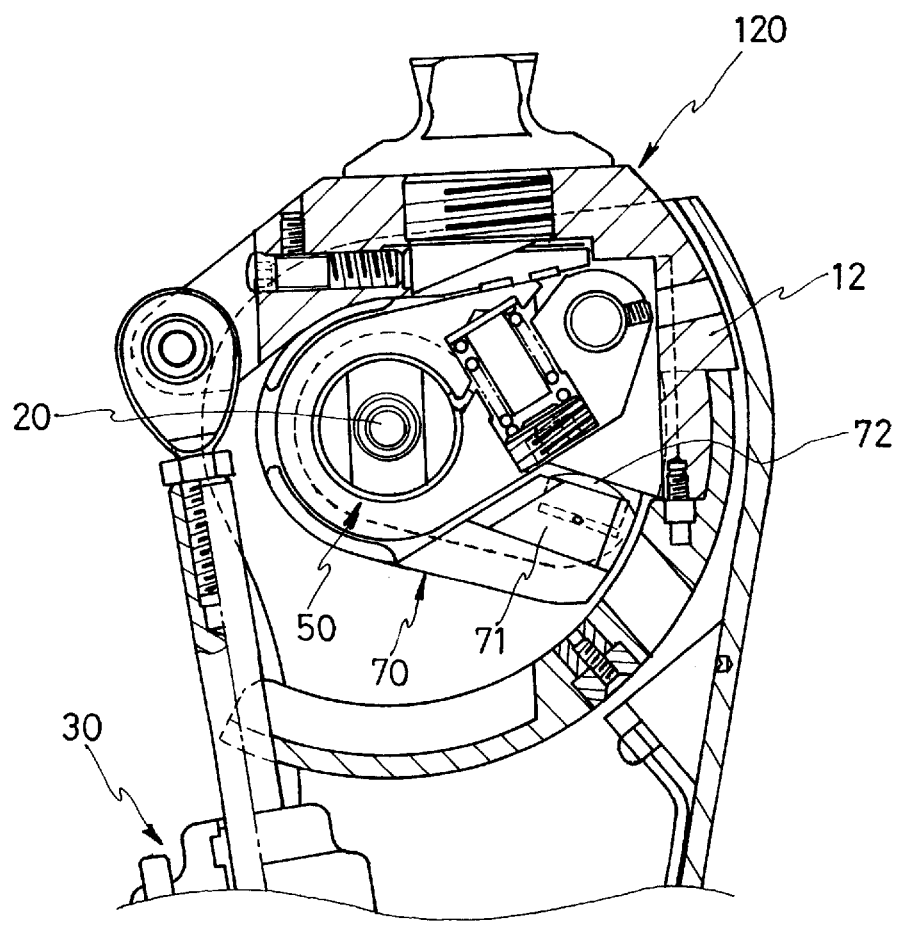
FIG. 5 is a straightened state view similar to FIG. 3 and is a sectional view of a main portion showing a completely extended state of the knee.
Figure 6:
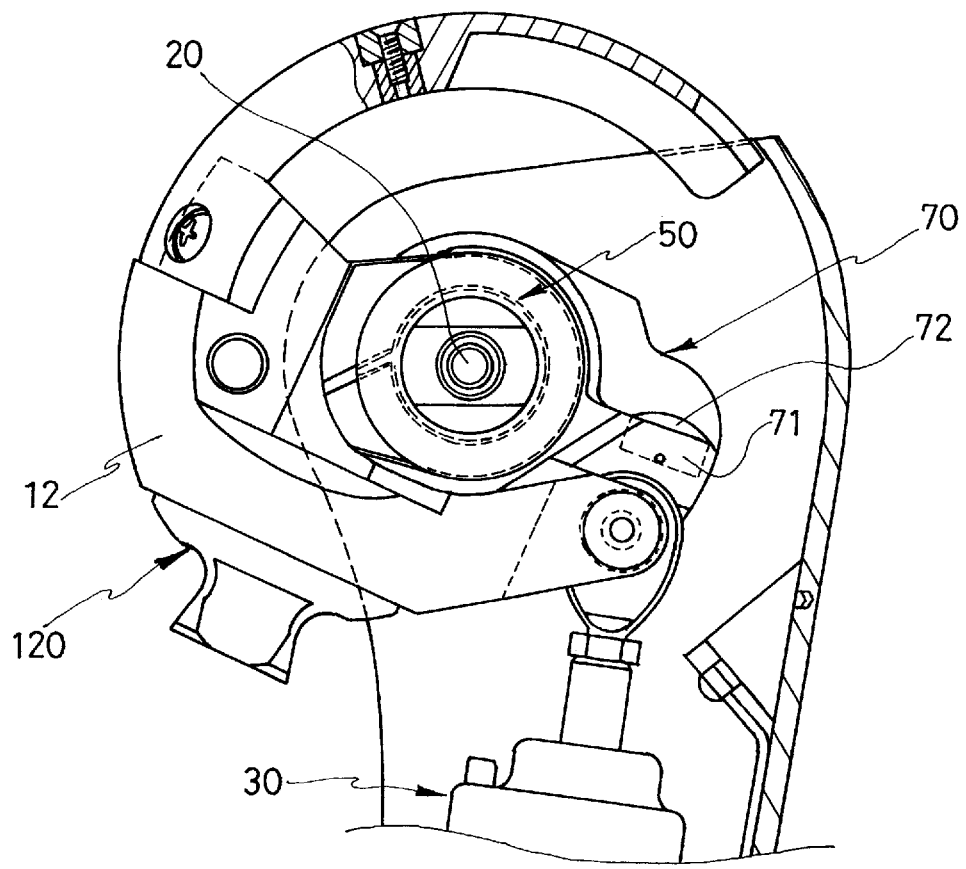
FIG. 6 is a sectional view of a main portion showing a maximum bent state of the knee.

Since the thigh prosthetic leg 10 is of a construction in which the upper member 120 and the lower member 140 can freely rotate about the knee axis 20, it is necessary to provide an appropriate braking force which is in conformity of a load of the user. The thigh prosthetic leg 10 includes a brake means 50 around the knee axis 20. This brake means 50 is of a type that a braking force is generated by reducing the diameter of a through-hole 52b of a brake block 52 which is embraced by the knee axis 20. The brake means of this type is known as disclosed, for example, in U.S. Pat. No. 3,863,274 (corresponding to Japanese Patent Publication No. 46432/1977). The brake block 52 is made of a titanium alloy. The brake block 52 is provided not only with a large though-hole 52b for inserting the knee axis 20 therein but also with a small through-hole 52s near an end portion thereof on the opposite side to the large through-hole 52b. The brake block 52 is set to the inner side of the knee plate 12 with the knee axis 20 inserted into the large through-hole 52b through a metal bush 53 and with a connecting pin 60 inserted into the small through-hole 52s. Opposite end portions of the knee axis 20 are supported respectively by bearing members 70 which are secured respectively to opposite sides of the frame 14. Opposite end portions of the connecting pin 60 are supported within a support hole formed in the knee plate 12. As means for firmly securing the bearing members 70 to the frame 14, the technology disclosed in British Laid Open Patent Application No. 2,296,442 (corresponding Japanese Laid-Open Patent Application No. 229055/1996) can be employed in which a non-circular hole is formed in each side of a frame 14 and a bearing member 70 made of metal is press-fitted into the hole by cool-fit. Since this technology can provide a highly reliable fixture, each bearing member 70 can be utilized as a stopper against bending or extending of the knee. For example, there can be obtained a stopper function in an extended state of the knee by forming a stopper portion 71 on the bearing member 70, then attaching a stopper rubber 72 for cushioning a shock thereto, and then abutting the stopper rubber 72 against the knee plate 12 (FIG. 5). Similarly, there can be obtained a stopper function in a bending state of the knee by abutting the stopper portion 71 provided on the bearing member 70 against another portion (for example, portion for supporting the second pin) of the knee plate 12 (FIG. 6). Here, the knee plate 12 is designed to rotate 140 degrees after the knee is completely extended until the knee is bent maximum.

Figure 7:
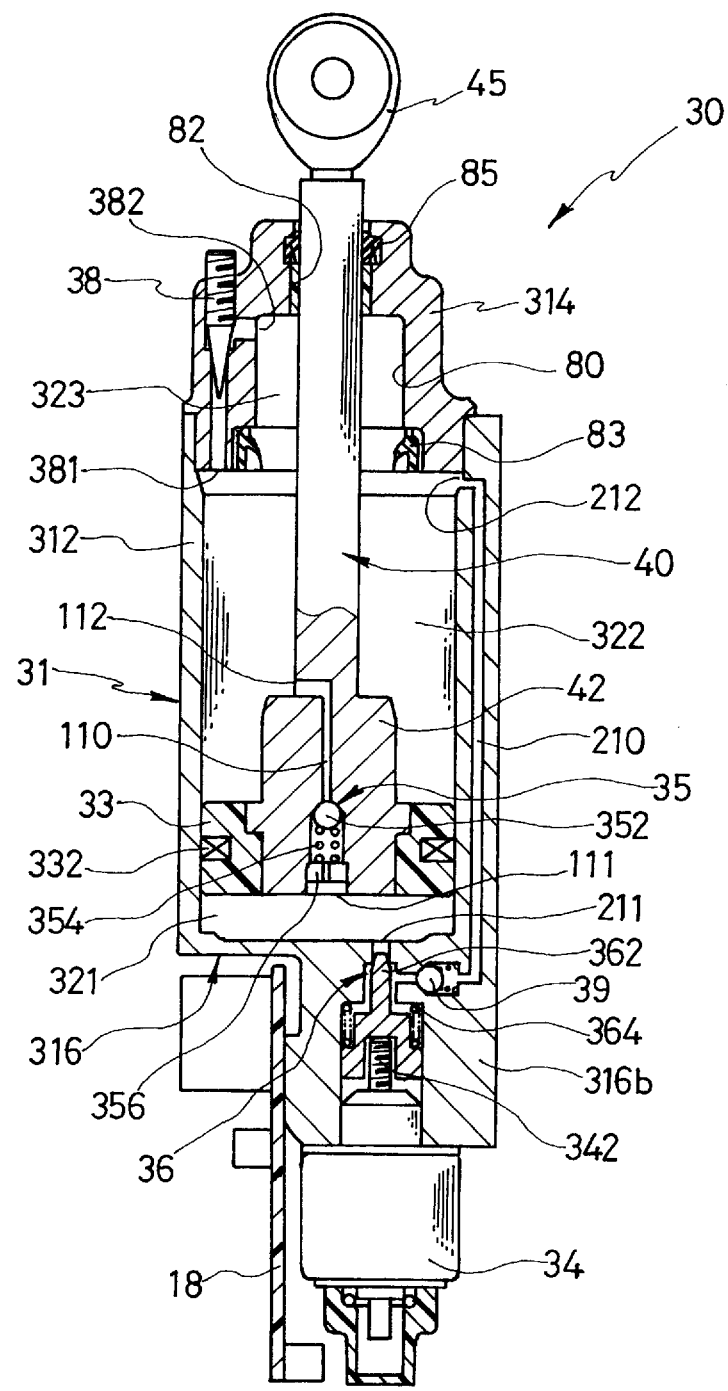
FIG. 7 is a sectional view showing the detail of an air cylinder device.

The thigh prosthetic leg 10 includes an air cylinder device 30 as a walk assisting means. The air cylinder device 30 may be similar to one which is disclosed in U.S. Pat. No. 5,405,407 or Japanese Laid-Open Patent Application No. 551/1997. FIG. 7 shows an overall construction of the air cylinder device 30. The air cylinder device 30 includes a sleeve-like cylinder body 31 which is made of an aluminum alloy or a synthetic resin. The cylinder body 31 includes a cylinder tube 312 having a uniform inside diameter, and covers 314, 316 located respectively on opposite end portions of the cylinder tube 312. The rod cover 314, through which the rod 40 penetrates, is provided not only with a reduced diameter hole 82 for guiding the rod 40 but also with an inner hole 80 having an intermediate diameter with respect to the reduced diameter hole 82 and the inside diameter of the cylinder tube 312. The cover 316 located on a bottom side of the cylinder body 31 includes a thick wall portion 316b which is located at a position radially outwardly offset from the axis of the cylinder tube 312. There is a fluid flow path 210 which starts at the thick wall portion 316b, passes through the cylinder tube 312 and opens at an inner periphery near the rod cover 314.

This thick wall portion 316b contains a variable throttle valve 36. This variable throttle valve 36 includes a poppet type valve element 362 made of a stainless steel, and a valve spring 364 for biasing the valve element 362 in a direction for opening the valve 36. The valve spring 364 is caused to abut against one end portion of a shaft 342 of a drive motor 34 consisting of a stepping motor under the effect of the valve spring 364. The drive motor 34 includes therein a screw mechanism for transforming a rotational motion to a linear motion. The shaft 342 is moved axially forwardly and backwardly by the screw mechanism. Accordingly, the shaft 342 of the drive motor 34 is capable of moving the valve element 362 forwardly and backwardly, thereby the degree of opening of the variable throttle valve 36 can be adjusted. The electronic substrate 18 generates a control signal in conformity with the speed of walking. This control signal is output to the drive motor 34 so that the degree of opening of the variable throttle valve 36 is appropriately adjusted.

On the other hand, the piston 33 made of a synthetic resin is axially movably fitted into the interior of the cylinder tube 312 of the cylinder body 31. The piston 33 retains on an outer periphery thereof a piston ring 332, thereby two front and rear chambers are defined. A first chamber 321 is located on the bottom side where the thick wall portion 316b is located, and a second chamber 322 is located on the rod cover 314 side. It should be designed such that when the piston 33 slides within the cylinder tube 312, openings 211, 212 at opposite ends of the fluid flow path 210 are not closed by the piston 33. The piston 33 is provided with a piston rod 40 integral therewith. The rod 40 penetrates through the rod cover 314 and projects outwardly of the cylinder body 31. That part (end portion 45) of the rod 40, which is located outside the cylinder body 31, serves to support the second pin. The rod 40 has an enlarged diameter portion 42 adjacent to the piston 33. The diameter of the enlarged diameter portion 42 is almost in match with the diameter of the inner hole 80 formed in the inner periphery of the rod cover 314. The inner hole 80 is provided at the opening portion and the reduced diameter portion 82 with lip type seal rings 83, 85, respectively. Owing to this arrangement, when the enlarged diameter portion 42 enters the interior of the inner hole 80 at a final stage of extending of the knee, a third chamber 323 is defined within the inner hole 80 by the enlarged diameter portion 42.

When attention is paid to the piston rod 33 and the enlarged diameter portion 42, there is another fluid flow path 110 which starts at one opening 111 of a surface of the piston 33, then penetrates the piston 33 and the enlarged diameter portion 42, and arrives at the other opening 112 of the reduced diameter portion of the rod 40. This fluid flow path 110 is provided on a midway thereof with a check valve 35. The check valve 35 includes a ball valve element 352, a valve spring 354 for biasing the ball valve element 352 in a valve closing direction towards a valve seat, and a support ring 356 for supporting the valve spring 354. The check valve 35 causes an air to flow from the second chamber 322 to the first chamber 321 through the fluid flow path 110, so that the knee is extended smoothly. In addition, since there is also the fluid flow path 210 connected in parallel relation to the fluid flow path 110, the air flows smoothly from the second chamber 322 to the first chamber 321 when the knee is extended. When the enlarged diameter portion 42 enters the interior of the inner hole 80 of the rod cover 314 in such a manner as to close the inner hole 80 before the knee is completely straightened, it defines the third chamber 323 within the inner hole 80. The enlarged diameter portion 42 further defines a cushion chamber around the enlarged diameter chamber 42.

In the air cylinder device 30, a stationary diaphragm 38 is connected in serial relation to the check valve 35 of the fluid flow path 110 at a prescribed stage before the knee is completely extended. The stationary diaphragm 38 consists of a screw-in type needle valve. The degree of opening of the stationary diaphragm 38 can be established by appropriately screwing the needle valve. Accordingly, it is preferred that the stationary diaphragm 38 is preliminarily adjusted to establish the degree of opening of the valve before the prosthetic limb is used taking individual differences into consideration. An additional fluid flow path is formed within the rod cover 314. One opening 381 of this additional fluid flow path is in communication with the fluid flow path 110 through the third chamber 323, and the other opening 382 is in communication with the second chamber 322 (namely, cushion chamber). The stationary diaphragm 38 is disposed in the midway of this fluid flow path. According to the air cylinder device 30, since not only the other opening 382 of the additional fluid flow path but also the opening 212 of the fluid flow path 210 are opened to the cushion chamber, there can be obtained not only a cushioning action caused by the stationary diaphragm 38 but also a cushioning action caused by the variable throttle valve 36. The air cylinder device 30 includes a restrictor 39 consisting of a check valve. The restrictor 39 is placed near the opening 211 of the fluid flow path 210. The restrictor 39 restricts only the flow coming from the second chamber 322 and proceeding towards the first chamber 321. Owing to a provision of the restrictor 39, the air cylinder device 30 has such advantage that a larger cushioning force is generated when the speed of walking is high.

The air cylinder device 30 is set up within the frame 14 by being connected to the lower member 140 and the upper member 120 respectively by pins with its rod 40 side up. For connecting the air cylinder device 30 to the lower member 140, one pair of trunnion pins 1400 are supported on opposite sides of the frame 14 of the lower member 140 such that the trunnion pins 1400 face each other. Then, a distal end of each trunnion pin 1400 is connected to the cover 316 portion of the cylinder tube 312 through a pivot. Accordingly, each trunnion pin 1400 corresponds to the afore-mentioned first pin and the center of each pin 1400 corresponds to the center P1. For connecting the air cylinder device 30 to the upper member 120, one end (rod end) of the rod 40 is disposed at an U-shaped portion 12u, in section, of the knee plate 12, and the portion 12u and the rod end 45 is rotatably connected through a clevis pin 1200. The clevis pin 1200 itself consists of a bolt and a nut. Through threading engagement between the bolt and the nut, the portion 12u of the knee plate 12 and the end portion 45 of the rod 40 can be connected together. Therefore, the clevis pin 1200 corresponds to the second pin and the center of the clevis pin 1200 corresponds to the center P2. According to a first feature of the present invention, the clevis pin 1200 is disposed at a position rotated 30 degrees upwardly from the contact point T of FIG. 1. This angle 30 degrees is, of course, a half of 60 degrees which is a swinging angle in a normal walking phase.

Figure 8:
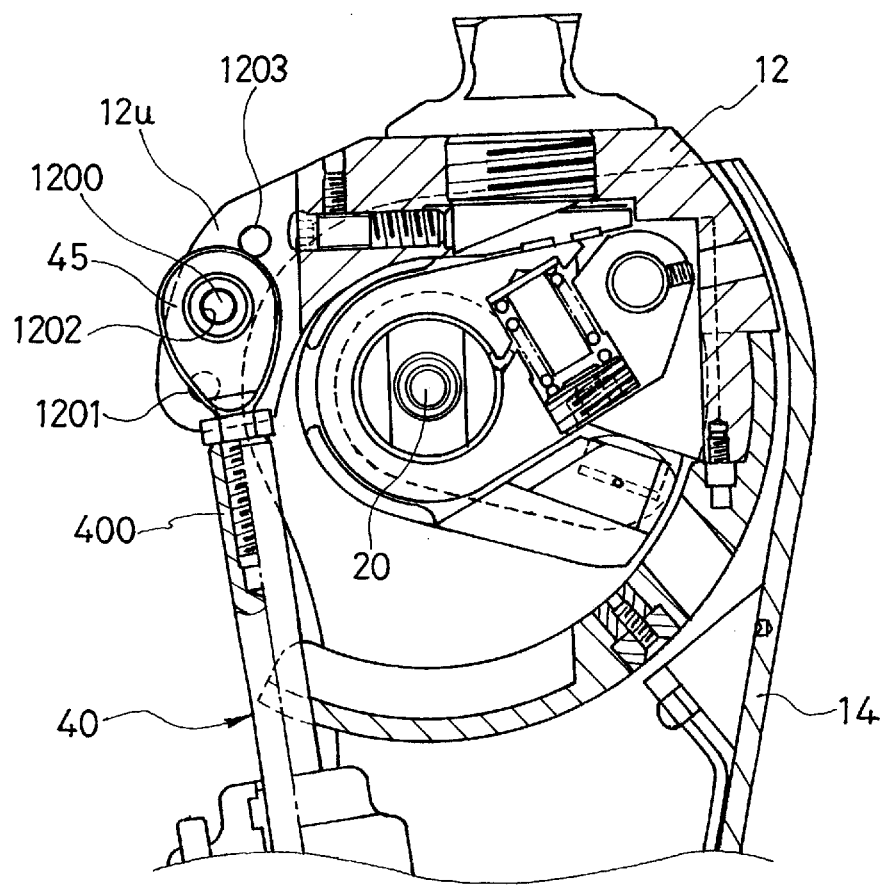
FIG. 8 is a sectional view showing a main portion of a prosthetic limb including a pin position change means of a first example.
Figure 9:
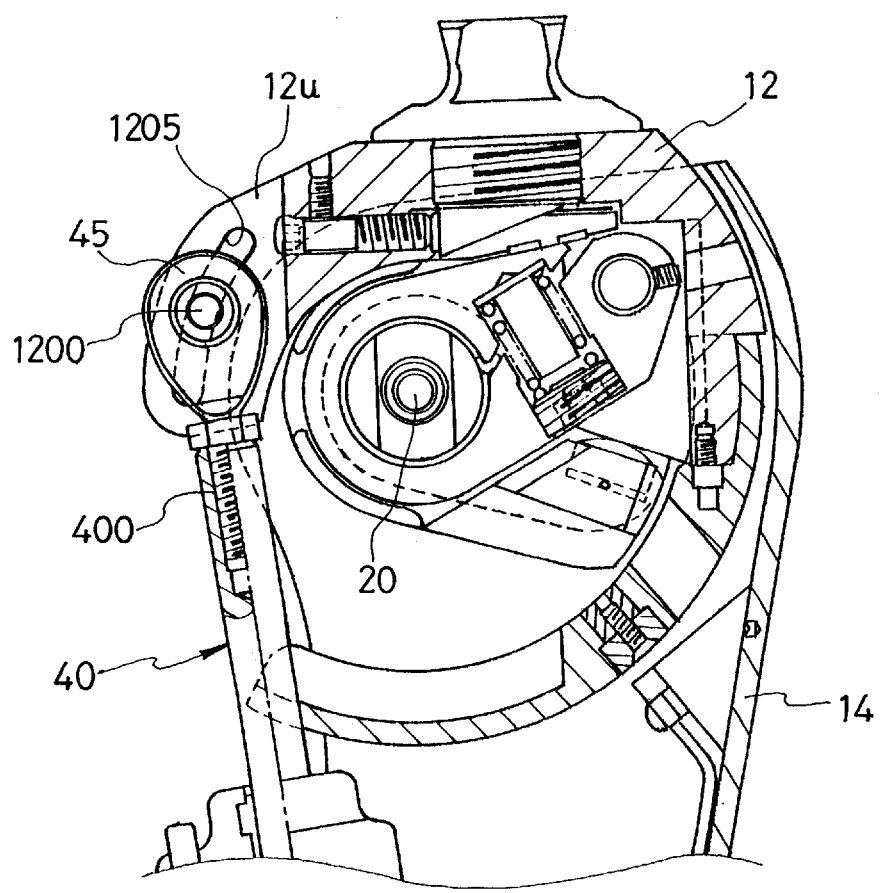
FIG. 9 is a sectional view showing a main portion of a prosthetic limb including a pin position change means of a second example.

According to a second feature of the present invention, the air cylinder device 30 includes a position change means capable of changing the position of the clevis pin 1200 in conformity with the speed of walking. In the pin position change means of the first example of FIG. 8, three attachment holes 1201, 1202, 1203 are formed in the portion 12u of the knee plate 12. The clevis pin 1200 is attached to selected one of the three attachment holes 1201, 1202, 1203. The three attachment holes 1201, 1202 and 1203 are located on a circular arc about the knee axis 20. Then, the middle attachment hole 1202, for example, is arranged to correspond to a position rotated 30 degrees upwardly from the contact point T of FIG. 1 (i.e., correspond to a swinging angle of 60 degrees corresponding to a normal walking), the upper attachment hole 1203 is arranged to correspond to a larger swinging angle than normal, and the lower attachment hole 1201 is arranged to correspond to a smaller swinging angle than normal. It is, of course, accepted that when the user makes a physical exercise, the lower attachment hole 1201 is arranged to correspond to a normal swinging angle of 60 degrees, and the remaining two attachment holes 1202, 1203 are arranged to correspond to swinging angles of 70 degrees and 80 degrees, respectively. In the second pin position change means of FIG. 9, an elongate hole 1205 is provided instead of the three attachment holes 1201, 1202, 1203 of the first example. The elongate hole 1205 has a configuration which can be exhibited when the three attachment holes 1201, 1202, 1203 are in mutual communication. In the second example, therefore, the attaching position of the clevis pin 1200 corresponding to the elongate hole 1205 may be successively changed over the whole range of the swinging angles of from 60 degrees to 80 degrees, for example. Since the body and the end portion 45 of the rod 40 are length-adjustably connected together through a threaded portion 400, any change in attaching position of the clevis pin 1200 can appropriately be met utilizing this threaded portion 400.

Figure 10:
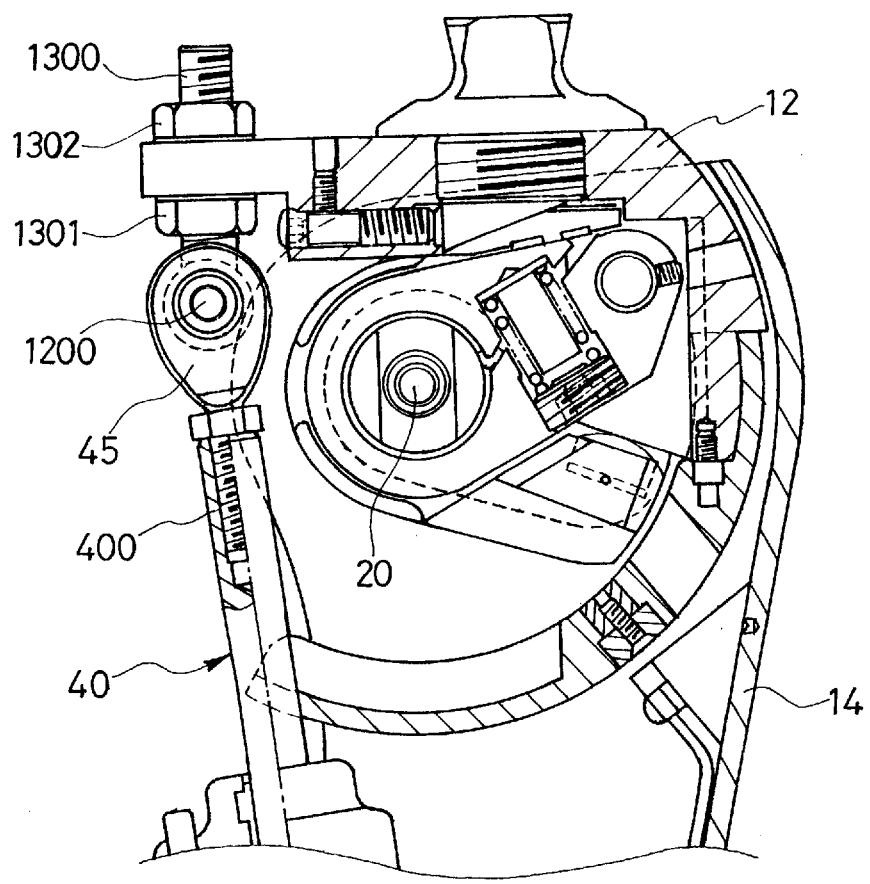
FIG. 10 is a sectional view showing a main portion of a prosthetic limb including a pin position change means of a third example.

In the third pin position change means of FIG. 10, the position of the clevis pin 1200 can successively be changed by a different construction from that of the second example. In the third pin position change means, the knee plate 12 is provided with an attaching bolt 1300 by which the clevis pin 1200 is supported. One pair of nuts 1301, 1302 are threadingly engaged with the attaching bolt 1300. Owing to this arrangement, the attaching bolt 1300 can be moved upwardly and downwardly by changing the engaging positions of the nuts 1301, 1302. Therefore, the position of the clevis pin 1200, which is in unison with the attaching bolt 1300, can appropriately be changed in accordance with the movement of the attaching bolt 1300.

Figure 11:
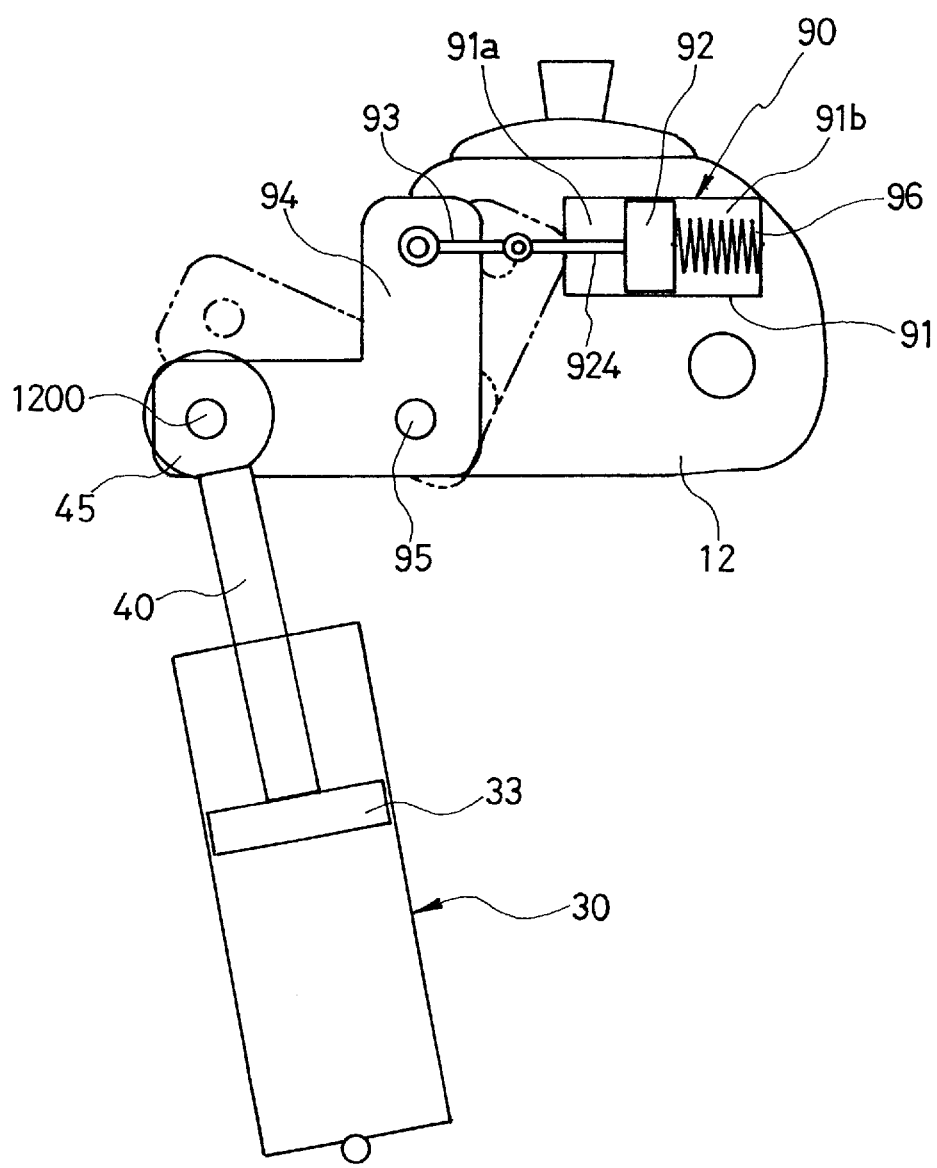
FIG. 11 is a schematic view showing a construction of a prosthetic limb including a pin position change means of another type.

According to the third feature of the present invention, in order to automatically change the position of the clevis pin 1200 without a need of manual operation, the knee plate 12 side is provided with a hydraulic cylinder 90. In an example of FIG. 11, a cylinder body 91 of the hydraulic cylinder 90 is secured to the knee plate 12. A piston 92 is movably disposed within the cylinder body 91 thus secured. A rod 924 extends from the piston 92. One end of the rod 924 is connected to one end of an L-shaped lever 94 through a connecting rod 93. The L-shaped lever 94 is capable of swinging about a support pin 95. The clevis pin 1200 is disposed at the other swinging end of the lever 94. As previously mentioned, the clevis pin 1200 is located on the end 45 of the rod 40 extending from the piston 33 of the air cylinder device 30.

Figure 12:
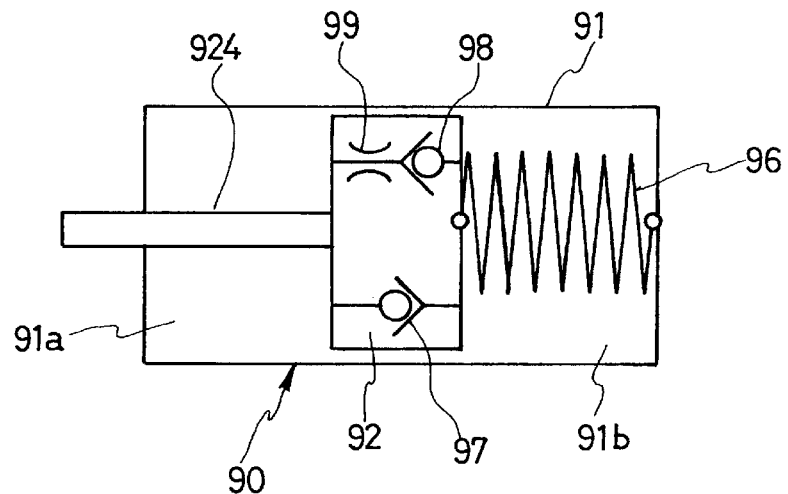
FIG. 12 is a schematic view showing an internal construction of a hydraulic cylinder to be used in the prosthetic limb of FIG. 11.

The air cylinder device 30 generates a repulsive force (this repulsive force cyclically varies in accordance with the cycle of walking and its maximum value becomes larger as the speed of walking is increased) in conformity with the speed of walking. The repulsive force is applied to the piston 92 of the hydraulic cylinder 90 through the connecting rod 93 and the rod 924. As a consequence, the piston 92 is changed in position in accordance of the largeness of the repulsive force, namely, in accordance with the speed of walking. In other words, the position of the clevis pin 1200 is automatically changed in accordance with the speed of walking. The piston 92 of the hydraulic cylinder 90 partitions the interior of the cylinder body 91 into a left chamber 91*a* and a right chamber 91*b*. The piston 92 is normally subjected to a force towards the left chamber 91*a* by a spring 96. Accordingly, the piston 92 is maintained still in a vicinity of a position where the force of the spring 96 and the repulsive force of the air cylinder device 30 are well balanced. As shown in FIG. 12, the piston 92 of the hydraulic cylinder 90 has two internal paths. The left chamber 91*a* and the right chamber 91*b* are communicated with each other through the two internal paths. One of the two internal paths is provided with a check valve 97. This check valve 97 prohibits a flow from the left chamber 91*a* to the right chamber 91*b* and allows a flow from the right chamber 91*b* to the left chamber 91*a*. The other internal path is provided with a check valve 98 and a throttle valve 99. The throttle valve 99 restricts the flow rate, and the check valve 98 prohibits a flow from the right chamber 91*b* to the left chamber 91*a* and allows a flow from the left chamber 91*a* to the right chamber 91*b*.

When the speed of walking is increased, the force of the spring 96 and the repulsive force from the air cylinder device 30 go out of balance. Since the oil in the right chamber 91*b* flows to the left chamber 91*a* through the internal paths including the check valve 97 during the time a larger force than that of the spring 96 acts, the piston 92 moves rightwardly in FIG. 12. In contrast, in case the force acting on the piston 92 is smaller than that of the spring 96, the force of the spring 96 acts on the piston 92 to move it leftwardly. However, the flow from the left chamber 91*a* to the right chamber 91*b* within the internal paths including the check valve 98 and the throttle valve 99 is restricted by the throttle valve 98, and therefore, a quantity of movement of the oil is small. As a consequence, the piston 92 gradually moves rightwardly and stops still in the vicinity of the position where the force acting on the piston 92 and the force of the spring 96 are balanced. On the other hand, when the speed of walking is decreased, the maximum value of the force acting on the piston 92 is decreased, and therefore, the piston 92 gradually moves leftwardly by the same reason as just mentioned and stops still in the vicinity of the position where the force acting on the piston 92 and the force of the spring 96 are balanced. By utilizing such characteristics of the hydraulic cylinder 90, the attaching position of the clevis pin 1200 of the end portion 45 of the rod 40 of the air cylinder device 30 can successively be changed.

Figure 13:
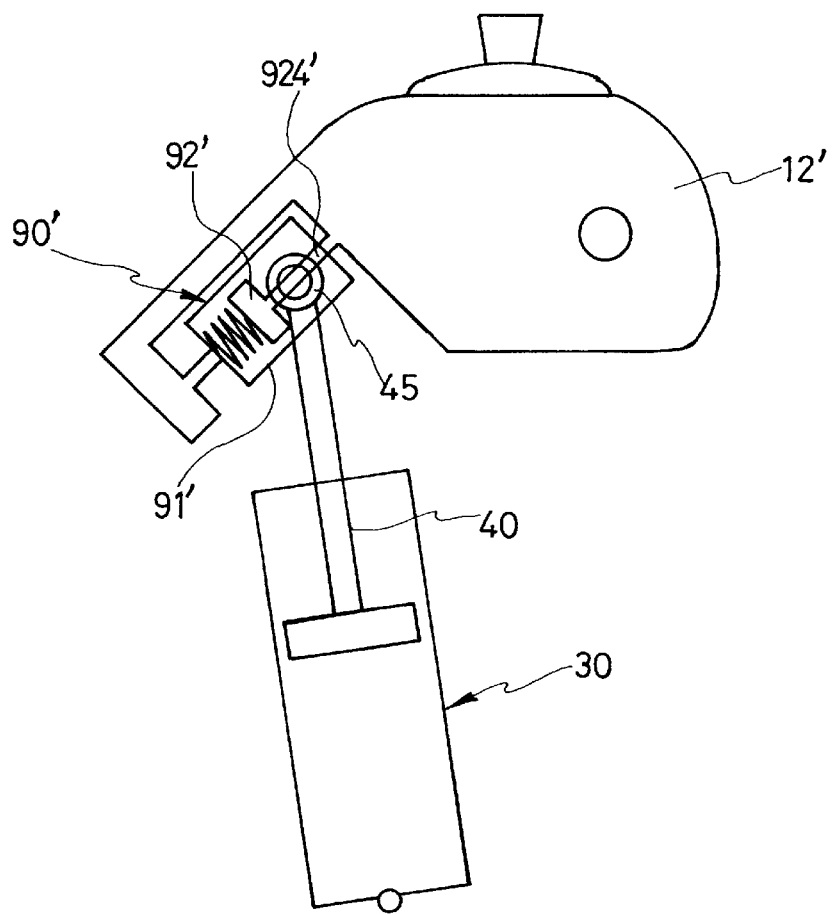
FIG. 13 is a schematic view showing a modified embodiment of the prosthetic limb of FIG. 11.

As shown in FIG. 13, a piston 92' and a rod 924' of a hydraulic cylinder 90' may be secured to a knee plate 12' so that a cylinder body 91' is moved. In this case, one end 45 of a rod 40 of the air cylinder device 30 is connected to a moving cylinder body 91'.

Responsibility of the hydraulic cylinders 90, 90' to the speed of walking depends on the degree of opening of the throttle valve 99 which is disposed in a midway of the internal path. Accordingly, in order to enhance the responsibility, the degree of opening of the throttle valve 99 can be electronically controlled. Specifically, the speed of walking is input into a micro computer and the degree of opening of the throttle valve 99 is varied in accordance with a pre-installed program.

What is claimed is:

1. An artificial limb including an air cylinder comprising an upper member including a knee plate to which a load of a user is applied, a lower member connected to said upper member at a knee portion, a knee axis for rotatably connecting said upper member and said lower member together, an air cylinder device disposed between and connected to said upper member and said lower member and adapted to assist in walking of the user through a stroke in accordance with bending and extending actions of the knee portion, a first pin for rotatably connecting one end of said air cylinder device to said lower member, and connecting means for connecting the other end of said air cylinder device to said upper member, said connecting means including a second pin located at the other end of said air cylinder device, a hydraulic cylinder supported by said upper member and adapted to change the position of an internal piston in conformity with the speed of walking, and a link mechanism for linking said hydraulic cylinder and said second pin together.

2. An artificial limb according to claim 1, wherein said air cylinder device becomes small in cylinder length when the knee portion is bent and large when the knee portion is extended.

3. An artificial limb according to claim 1, wherein said air cylinder device includes a sleeve-like cylinder body, a piston disposed within said cylinder body and adapted to partition the interior of said cylinder body into a first chamber on a bottom side and a second chamber on a head side, and a rod one end of which is integral with said piston and the other end of which extends outwardly from the head side of said cylinder body.

4. An artificial limb according to claim 1, wherein said second pin is located at one end of said rod behind the knee portion.

5. An artificial limb according to claim 4, wherein said lower member includes a hollow frame, and a cylinder body of said air cylinder device is inserted into the hollow interior of said frame.

6. An artificial limb according to claim 1, wherein a range of swinging of said second pin caused by walking of the user is from about 60 degrees to about 80 degrees.

7. An artificial limb according to claim 1, wherein a range of swinging of said second pin is about 60 degrees when it corresponds to the speed of from a slow walking to a normal walking, about 70 degrees when it corresponds to the speed of a quick walking, and about 80 degrees when it corresponds to the speed of run with small steps.

8. An artificial limb according to claim 1, wherein said first pin is a trunnion pin, and said second pin is a clevis pin.

9. An artificial limb according to claim 1, further comprising brake means disposed about said knee axis and adapted to generate a braking force in accordance with a load applied through said knee plate.

10. An artificial limb according to claim 1, wherein said hydraulic cylinder is subjected to a force coming from said air cylinder device through said second pin, and successively changes the position of said internal piston such that said internal piston moves away from said first pin.

\* \* \* \* \*